United States Patent
Baudino

(10) Patent No.: US 10,881,850 B2
(45) Date of Patent: Jan. 5, 2021

(54) SELF-TUNNELING LEAD

(71) Applicant: Medtronic, Inc., Minneapolis, MN (US)

(72) Inventor: Michael D. Baudino, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 199 days.

(21) Appl. No.: 13/749,489

(22) Filed: Jan. 24, 2013

(65) Prior Publication Data

US 2013/0238067 A1 Sep. 12, 2013

Related U.S. Application Data

(60) Provisional application No. 61/607,248, filed on Mar. 6, 2012.

(51) Int. Cl.
*A61N 1/05* (2006.01)

(52) U.S. Cl.
CPC ......... *A61N 1/0502* (2013.01); *A61N 1/0504* (2013.01); *A61N 1/0551* (2013.01)

(58) Field of Classification Search
CPC .......... A61N 1/05; A61N 1/056; A61N 1/052; A61N 1/0502; A61N 1/0504; A61N 1/0553
USPC ....................................................... 607/116
See application file for complete search history.

(56) References Cited

U.S. PATENT DOCUMENTS

| | | | |
|---|---|---|---|
| 4,846,812 A | 7/1989 | Walker | |
| 5,135,786 A | 8/1992 | Hayashi | |
| 5,145,935 A | 9/1992 | Hayashi | |
| 5,266,669 A | 11/1993 | Onwunaka | |
| 5,439,966 A | 8/1995 | Graham | |
| 5,441,489 A | 8/1995 | Utsumi | |
| 5,634,913 A | 6/1997 | Stinger | |
| 7,146,222 B2* | 12/2006 | Boling | A61N 1/0531 607/116 |
| 7,283,866 B2* | 10/2007 | Mumford | A61B 5/0492 600/546 |
| 7,437,197 B2 | 10/2008 | Harris et al. | |
| 7,499,755 B2 | 3/2009 | Cross, Jr. | |
| 7,655,014 B2 | 2/2010 | Ko et al. | |
| 2005/0085870 A1 | 4/2005 | Goroszeniuk | |
| 2005/0182470 A1 | 8/2005 | Cross | |
| 2005/0209667 A1* | 9/2005 | Erickson | A61B 5/0422 607/116 |

(Continued)

FOREIGN PATENT DOCUMENTS

WO WO2007/085822 8/2007

OTHER PUBLICATIONS

Zdrahala et al., "Softening of Thermoplastic Polyurethanes: A Structure/Property Study," Journal of Biomaterials Applications, Oct. 1987, vol. 2, No. 4, pp. 544-561 (abstract only).

*Primary Examiner* — Mallika D Fairchild
*Assistant Examiner* — Minh Duc G Pham
(74) *Attorney, Agent, or Firm* — Mueting Raasch Group

(57) ABSTRACT

An implantable medical lead includes (i) a proximal end portion including a contact and having a proximal end; and (ii) a distal end portion including an electrode and having a distal end. The electrode is electrically coupled to the contact. The distal end portion is generally flat and sufficiently stiff to be pushed through subcutaneous tissue.

18 Claims, 7 Drawing Sheets

(56) References Cited

U.S. PATENT DOCUMENTS

2006/0247749 A1\* 11/2006 Colvin .................... A61N 1/05
607/116
2010/0076535 A1  3/2010 Pianca et al.
2011/0054581 A1\* 3/2011 Desai ...................... A61N 1/05
607/116

\* cited by examiner

SELF-TUNNELING LEAD

FIELD

The present disclosure relates to implantable medical devices; more particularly to medical leads capable of delivering electrical signals to tissue of a patient, such as a nerve.

BACKGROUND

Implantable medical systems that include an implantable electrical signal generator device and one or more implantable medical leads have been used to treat a variety of diseases and disorders, such as Parkinson's disease, essential tremor, obsessive-compulsive disorder, pain, nausea and vomiting, and incontinence. With such systems, the electrical signal generator device, often referred to as an implantable pulse generator or IPG, is implanted in subcutaneous tissue of a patient, such as in the abdomen, buttocks, chest, or the like, at a distance from the therapeutic target, such as the brain, spinal cord, gastrointestinal tract or the like. Leads carry electrical signals generated by the IPG to the therapeutic site once operably coupled to the IPG and properly positioned relative to the therapeutic site.

Leads are typically implanted through the use of an introducer and stylet. The introducer is used to tunnel a subcutaneous path from the site of implantation of the IPG to, or near, the target site. The lead is then passed through a lumen of the introducer, and thus through the subcutaneous path. A stylet may be inserted into a lumen of the lead to push the lead through the lumen of the introducer. The stylet is removed and the introducer is withdrawn over the lead. The lead implantation procedure can be time consuming and invasive.

BRIEF SUMMARY

The present disclosure, among other things, describes leads that are capable of being tunneled through subcutaneous tissue without the use of an introducer. The leads may be beneficially employed for electrical stimulation therapies in which cranial nerves or other peripheral nerves are targeted.

In an embodiment, an implantable medical lead includes (i) a proximal end portion including a contact and having a proximal end; and (ii) a distal end portion including an electrode and having a distal end. The electrode is electrically coupled to the contact. The distal end portion is generally flat or planar and sufficiently stiff to be pushed through subcutaneous tissue.

In an embodiment, an implantable medical system includes a lead and an implantable active electrical medical device operably couplable to the lead. The lead includes (i) a proximal end portion including a contact and having a proximal end; and (ii) a distal end portion including an electrode and having a distal end. The electrode is electrically coupled to the contact. The distal end portion is generally flat or planar and sufficiently stiff to be pushed through subcutaneous tissue.

In an embodiment, a method includes providing a lead having (i) a proximal end portion including a contact and having a proximal end; and (ii) a distal end portion including an electrode and having a distal end. The electrode is electrically coupled to the contact. The distal end portion is generally flat or planar and sufficiently stiff to be pushed through subcutaneous tissue. The method further includes pushing the generally flat or planar portion to advance the distal end through subcutaneous tissue of the subject until the electrode is properly positioned relative to a target area of the subject.

One or more embodiments of the leads, systems and methods described herein provide one or more advantages over prior leads, systems and methods. Such advantages will be readily understood from the following detailed description when read in conjunction with the accompanying drawings.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

As used herein, "providing" in the context of the present claims means to purchase, manufacture, assemble, or otherwise obtain.

The present disclosure describes, inter alia, leads that may be tunneled through subcutaneous tissue without the use of an introducer. Nearly any implantable medical device or system employing leads may be used in conjunction with the leads described herein. Representative examples of such implantable medical devices include hearing implants, cochlear implants; sensing or monitoring devices; signal generators such as cardiac pacemakers or defibrillators, neurostimulators (such as spinal cord stimulators, brain or deep brain stimulators, peripheral nerve stimulators, vagal nerve stimulators, occipital nerve stimulators, subcutaneous stimulators, etc.), gastric stimulators; or the like. For purposes of occipital nerve stimulation, electrical signal generators such as Medtronic, Inc.'s Restore® or Synergy® series of implantable neurostimulators may be employed.

Figure 1:
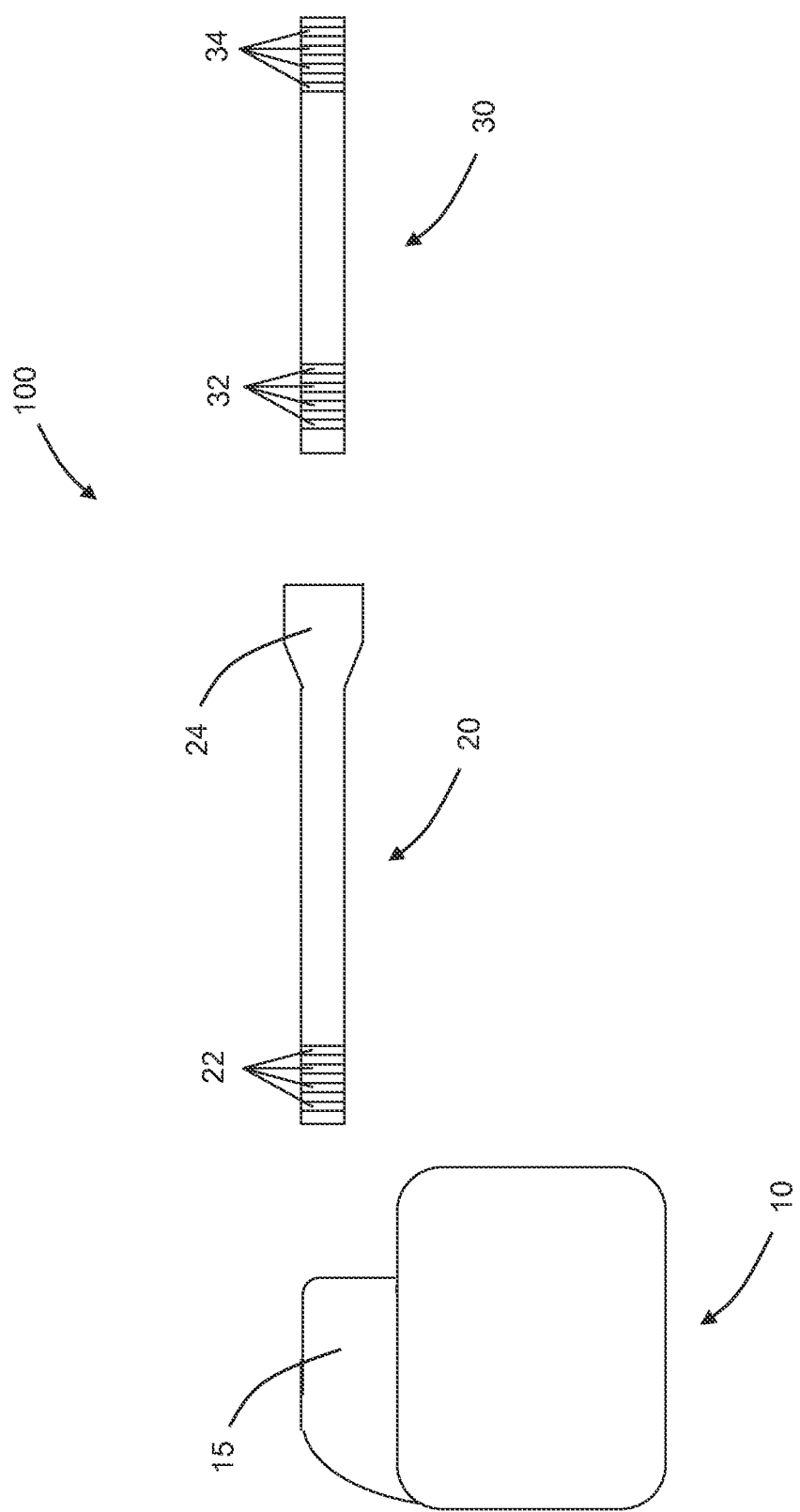
FIG. 1 is a schematic side view of an implantable system including an active implantable electrical medical device, a lead extension and a lead.

Referring to FIG. 1, a side view of an implantable electrical signal generator system 100 is shown. In the depicted system 100, the electrical signal generator 10 includes a connector header 15 configured to receive a proximal portion of lead extension 20. The proximal portion of lead extension 20 contains a plurality of electrical contacts 22 that are electrically coupled to internal contacts (not shown) at distal connector 24 of lead extension 20. The connector header 15 of the signal generator 10 contains internal contacts (not shown) and is configured to receive the proximal portion of the lead extension 20 such that the internal contacts of the connector header 15 may be electrically coupled to the contacts 22 of the lead extension 20 when the lead extension 20 in inserted into the header 15.

The system depicted in FIG. 1 further includes a lead 30. The depicted lead 30 has a proximal portion that includes a plurality of contacts 32 and a distal portion that includes a plurality of electrodes 34. Each of the electrodes 34 may be electrically coupled to a discrete contact 32. The distal connector 24 of the lead extension 20 is configured to receive the proximal portion of the lead 30 such that the contacts 32 of the lead 30 may be electrically coupled to the internal contacts of the connector 24 of the extension 20. Accordingly, a signal generated by the signal generator 10 may be transmitted to a patient by an electrode 34 of lead 30 when lead is connected to extension 20 and extension 20 is connected to signal generator 10.

It will be understood that lead 30 may be coupled to signal generator 10 without use of an extension 20. Any number of leads 30 or extensions 20 may be coupled to signal generator 10. Typically, one or two leads 30 or extensions 20 are coupled to signal generator 10. While lead 20 is depicted as having four electrodes 34 arranged in a linear fashion, it will be understood that lead 30 may include any number of electrodes 34, e.g. one, two, three, four, five, six, seven, eight, sixteen, thirty-two, or sixty-four, arranged in any fashion, such as 1×4 array, 2×4 array, 1×8 array, or the like. Corresponding changes in the number of contacts 32 in lead 30, contacts 22 and internal contacts in connector 24 of lead extension, or internal contacts in connector 15 of signal generator 10 may be required or desired.

Figure 2:
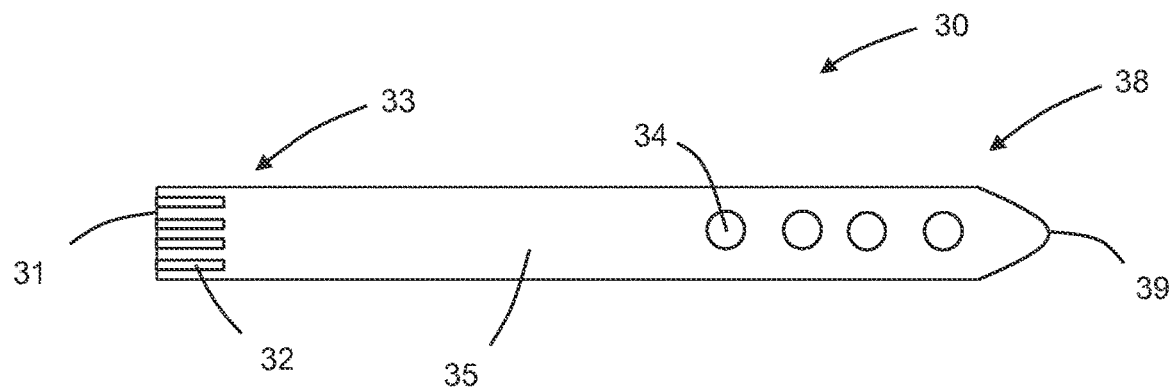
FIGS. 2-4 are schematic top views of various embodiments of leads described herein.
Figure 3:
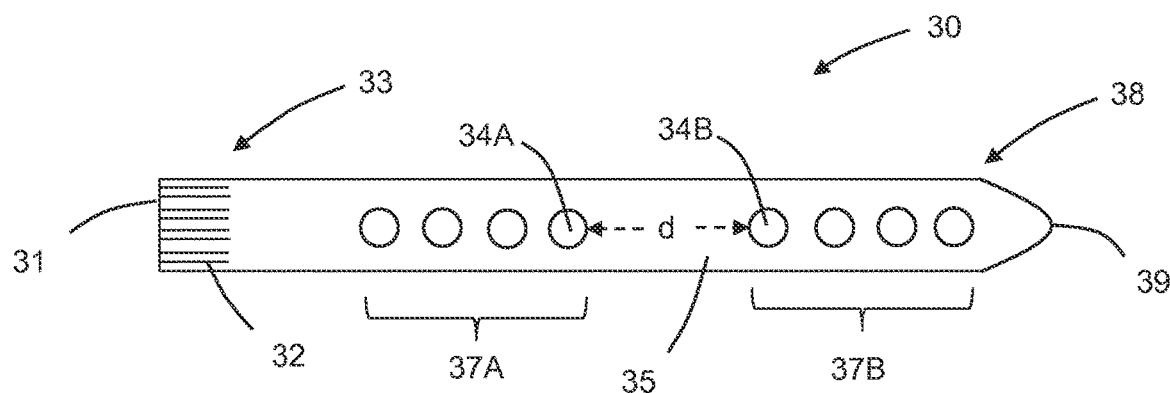
Figure 4:
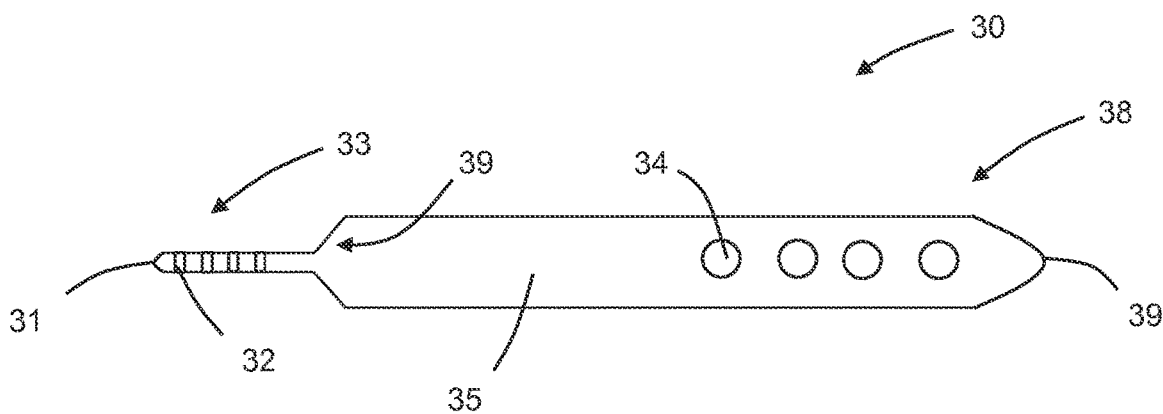

Referring now to FIGS. 2-4, schematic top views of leads 30 are shown. The leads 30 include a proximal end portion 33 having a proximal end 31 and a distal end portion 38 having a distal end 39, which is tapered in the depicted embodiments. The proximal end portion 33 includes contacts 32, and the distal end portion 38 includes electrodes 34 operably coupled to the contacts 32. The distal end portion 38 is formed from a generally flat or planar body 35, which (or portions of which) may be shaped in a manner similar to currently available paddle leads. In embodiments, the generally flat or planar body extends from the distal end 39 to the proximal end 31 (see, e.g. FIGS. 2-3). In embodiments, the generally flat or planar body 35 extends proximally from the distal end 39 to a transition section in proximity to the proximal end portion 33 (see, e.g., FIG. 4). In some embodiments, the generally flat or planar body 35 accounts for 70% or more, 80% or more, or 90% or more of the length of the lead 30.

In embodiments, electrodes 34 are exposed through only one surface (e.g., the major surface depicted in FIGS. 2-4) of the generally flat or planar body 35.

In embodiments, contacts 32 are exposed through only one surface (see, e.g., FIGS. 2-3) of the proximal end portion 33. Of course, the contacts may be exposed through both surfaces. In some of such embodiments, the proximal end portion 33 may include a ribbon contacts, flat or planar plate contact, or other planar-type contacts. In embodiments (see, e.g., FIG. 4), the contacts 34 are cylindrical ring-type contacts. Conductors (not shown) may electrically connect contacts 32 to electrodes 34. In embodiments (not shown), the contacts may be pins, or the like, that extend from the lead body 35 at the proximal end portion 33. Of course, any suitable contact and corresponding connector may be used.

The generally flat or planar body portion 35 of the lead 30 is sufficiently stiff to be pushed through subcutaneous tissue of a patient, such as hypodermis tissue that comprises mainly adipose tissue. As the length of the generally flat or planar body portion 35 increases the more difficult it may be to push the entire length of the body 35 through the subcutaneous tissue. Thus, in some embodiments, the length of the generally flat or planar body portion 35 is relatively small and is inserted through an incision made in close proximity to a target area of the subject in which one or more electrodes 34 are to be placed. Accordingly, the leads 30 described herein may be advantageously used for purposes of peripheral or cranial nerve stimulation where incisions may be made close to the nerve to be stimulated, the distal end 39 of the lead 30 may be advanced through subcutaneous tissue by pushing the generally flat or planar body member 35 until one or more electrodes 34 are properly positioned relative to the target nerve such that electrical stimulation therapy may be applied to the nerve via the electrode(s) 34.

It will be understood that implantation of a lead without the use of an introducer may result in more secure placement of the lead relative to the target tissue (relative to implantation with an introducer). Because an introducer has an outer dimension larger than that of the lead that it is configured to introduce, the introducer creates a tunnel through tissue, such as subcutaneous tissue, that is larger in diameter than the lead. The lead may then move about within the larger tunnel and may migrate over time. However, if the lead, or a portion thereof, is sufficiently stiff to be pushed through tissue without the use of an introducer, the tunnel created by the lead will be roughly the same outer dimension as the lead. Accordingly, the lead will have less room for movement (relative to when an introducer is used) and thus will be less likely to migrate over time.

In embodiments, the generally flat or planar body portion 35 of the lead 30 has a modulus of elasticity of 3000 pounds per square inch (psi) or greater (e.g, 3500 psi or greater, 4000 psi or greater, 4500 psi or greater, 5000 psi or greater, or 10,000 psi or greater) at room temperature and 50% relative atmospheric humidity. Examples of materials that may be used to form a body 35 having such a stiffness include nylon (about 400,000 psi), carbonate (about 320,000 psi), 75D polyurethane (about 4700 psi), or the like. By way of example, 65D polyurethane (about 2300 psi) may not be sufficiently stiff.

It will be understood that the design of the lead, in addition to the material forming the body of the lead may affect its ability to be pushed through subcutaneous tissue. For example, the thickness of the lead, and thus the material forming the lead body, may affect the ability to be pushed through subcutaneous tissue. If the lead body is too thin and is made of a material or materials having relatively low modulus of elasticity, the ability of the lead to be pushed through subcutaneous tissue may be compromised, while lead having thicker lead bodies made of the same material may be readily pushed through subcutaneous tissue. In addition or alternatively, the structural design of the lead body may affect its ability to be pushed through subcutaneous tissue (without prior tunneling or path creation). For example, if the lead is designed to have a solid lead body or a honeycomb-shaped design can affect the ability to be pushed through tissue. Such design considerations may also affect ability of the lead body to bend in the direction orthogonal to the pushing direction, which can affect patient comfort.

In embodiments, the body 35 is configured to become softer and more flexible following implantation, which may allow the body to conform to the shape of the tissue in which it is implanted, may result in less tissue erosion over time, or may result in improved patient comfort relative to bodies that do not become softer or more flexible following implantation. Any material that becomes softer or more flexible at body temperature (relative to room temperature) or at higher moisture (implanted relative to ambient) may be used. In embodiments, the body 35 may remain rigid for a period of time after implantation, such as between 2 minutes and 10 minutes, greater than 10 minutes, or the like, by altering the glass transition period of the material that forms the body 35. Examples of materials that may soften following implantation include polysaccharides, alginates, starch polymers, shape memory polyurethanes, hydrogels, temperature or fluid sensitive polyethylene oxide polymers or the like. Examples of polymeric materials that may soften or become more flexible upon implantation are described in, for example, U.S. Pat. Nos. 5,634,913; 5,266,669; 4,846,812; 5,441,489; 5,145,935; 5,135,786; and 5,439,966, which patents are hereby incorporated herein by reference in their entireties to the extent that they do not conflict with the disclosure presented herein. Additional information regarding softening thermoplastic polyurethanes can be found in Zdrahala et al., "Softening of Thermoplastic Polyurethanes: A Structure/Property Study," Journal of Biomaterials Applications, October 1987, vol. 2, no. 4, pp. 544-561, which is hereby incorporated herein by reference in its entirety to the extent that they do not conflict with the disclosure presented herein.

In embodiments, the generally flat or planar body member 35 of the lead has a modulus of elasticity of 3000 pounds per square inch (psi) or greater (e.g, 3500 psi or greater, 4000 psi or greater, 4500 psi or greater, 5000 psi or greater, or 10000 psi or greater) prior to being implanted in the patient (at room temperature and 50% ambient relative humidity) and has a modulus of elasticity after implantation in a subject that is 90% or less (e.g., 85% or less, 80% or less, 75% or less, 70% or less, 65% or less, 60% or less 55% or less, or 50% or less) of the modulus prior to being implanted. In embodiments, the modulus of elasticity after implantation is 3000 psi or less (e.g, 2500 psi or less, 2000 psi or less, 1500 psi or less, 1000 psi or less, or 500 psi or less) after implantation in a subject.

In embodiments, the generally flat or planar body member of the lead is configured to conform, to some extent, to its implanted shape. For example, if the body member is flat or planar prior to implantation, but curved after implantation, the body member may adopt the curved shape as its relaxed state or tend toward the curved state as its relaxed shape. Pressure due to tissue compression, temperature, humidity, or the like of the implant environment may cause the relaxed conformation state of the lead body to change with time; e.g. due to stress relief, creep, compression setting, or the like. Materials which are subject to such conformational relaxed state changes after implant by be desirably employed to reduce tissue erosion, or the like.

Referring again to FIGS. 2-4, the electrodes 34 may be disposed along generally flat or planar body 35 in any suitable manner. In the depicted embodiments, the electrodes 34 are generally linearly disposed along the body 35 but may be disposed in any other suitable manner. In embodiments (e.g., as depicted in FIG. 3), the lead 30 includes first 37A and second 37B arrays of electrodes. The electrodes in the arrays 37A, 37B may be linearly arranged as depicted in FIG. 3. In the depicted embodiment, the spacing between adjacent electrodes within the first 37A and second 37B arrays are substantially the same; however, the distance (d) between the most proximal electrode 34B of the second array 37B and the most distal electrode 34A of the first array 37A is predetermined such that the first array 37A may be positioned so that one or more electrodes may capture a first target (e.g., a left occipital nerve) and the second array 37B may be positioned so that one or more electrodes may capture a second target (e.g., a right occipital nerve). The anatomical locations of the targets for the electrodes of the first 37A and second 37B arrays may determine the distance between the most proximal electrode 34B of the second array 37B and the most distal electrode 34A of the first array 37A. In embodiments, the distance between the most proximal electrode 34B of the second array 37B and the most distal electrode 34A of the first array 37A is between about 2 centimeters and about 16 centimeters, such as between about 2 centimeters and 8 centimeters, or the like. Leads 30 with such spacing between electrode arrays may be advantageously used for stimulating a left occipital nerve with electrodes of one array 37A, 37B and stimulating a right occipital nerve with electrodes of the other array 37A, 37B (e.g., as discussed below with regard to FIGS. 9-10).

Figure 5:
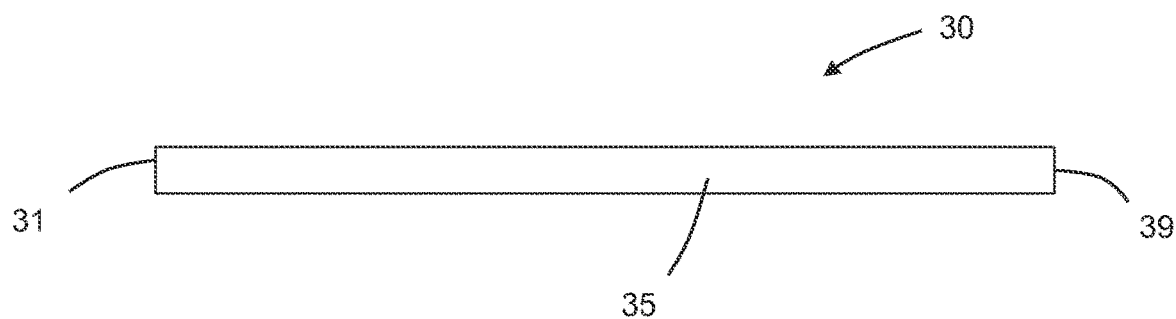
FIG. 5 is a schematic side view of an embodiment of a lead.

Referring now to FIG. 5, a side view of a lead 30 is shown. In the embodiment depicted, the generally flat or planar body 35 extends from the distal end 39 to the proximal end 31 (e.g., as in FIGS. 2-3). The body 35 may be of any suitable width (w). In embodiments, the body 35 has a generally constant width (w) along its length. In some embodiments (not shown) the distal end may be tapered to facilitate advancement through subcutaneous tissue. In embodiments, the width (w) of the generally flat or planar body member 35 is between 0.05 and 0.5 inches; e.g., between 0.2 and 0.4 inches, about 0.3 inches, or about 0.325 inches.

Figure 6:
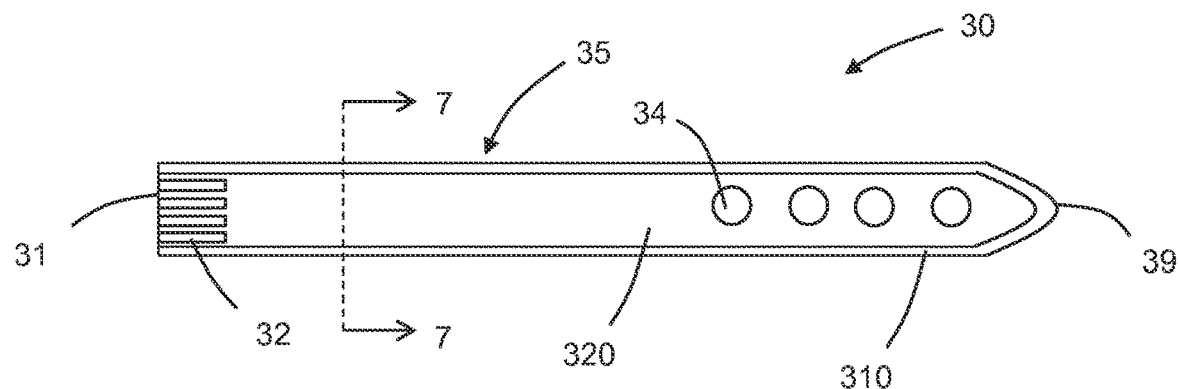
FIG. 6 is a schematic top vie of an embodiment of a lead.

Referring now to FIG. 6, in which like numbers refer to like components relative to previous figures, the generally flat or planar body 35 may have an outer periphery 310 and an inner region 320. In embodiments, the outer periphery 310 is more rigid than the inner region 320. The outer periphery 310 may be formed of materials and have properties similar to those described above with regard to body 35. The softer, more flexible inner region 320 may be made of any suitable material, such as silicone, lower density polyurethanes, and the like. In embodiments, the softer, more flexible inner region 320 has a modulus of elasticity of 2500 psi or less, of 2000 psi or less, of 1500 psi or less, of 1000 psi or less, or of 500 psi or less.

Figure 7:
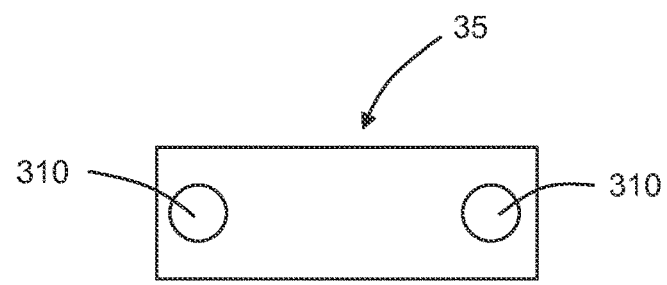
FIG. 7 is a schematic sectional view of an embodiment of a lead depicted in FIG. 6 taken through line 7-7.

In embodiments, the outer periphery 310 forms one or more lumens through which stiffening rods or stylets may be inserted to facilitate advancement of distal end 39 of lead through subcutaneous tissue. By way of example, FIG. 7 depicts a schematic sectional view of an embodiment of the lead of FIG. 6 taken through line 7-7. As shown in FIG. 7, lumens 330 configured to receive stiffening rods or stylets are formed in the periphery of the generally flat or planar lead body 35. For purposes of brevity and convenience, conductors that couple contacts to electrodes are not shown in FIG. 7.

Figure 8:
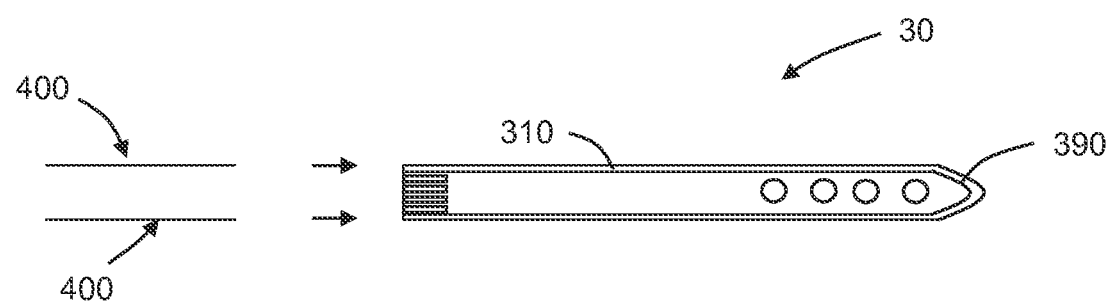
FIG. 8 is a schematic top view of an embodiment of a lead and associated stiffening rods.

As shown in FIG. 8, stiffening rods 400 may be inserted into lumens in the outer periphery 310 of lead 30 to facilitate implantation. The stiffening rods 400 or stylets may be removed after implanting the lead 30. The distal tip 390 of the lead 30 may be reinforced or be formed from material of sufficient strength to withstand pushing forces exerted by rods 400 as the lead 30 is advanced through subcutaneous tissue.

In embodiments, stiffening rods 400 are incorporated into the manufacture of the lead 30 and form a permanent part of the lead 30. Thus, the stiffening rods 400 may provide the outer periphery 310 with more rigidity than the inner portion.

The leads described herein may be used for any suitable purpose. As discussed above, the leads described herein may be advantageously used for purposes of peripheral nerve stimulation, which includes peripheral nerve field stimulation (PNFS) and subcutaneous stimulation (SQS). For purposes of example, a description of occipital nerve stimulation, e.g. for treatment of headache, with leads as described herein is provided below.

Figure 9:
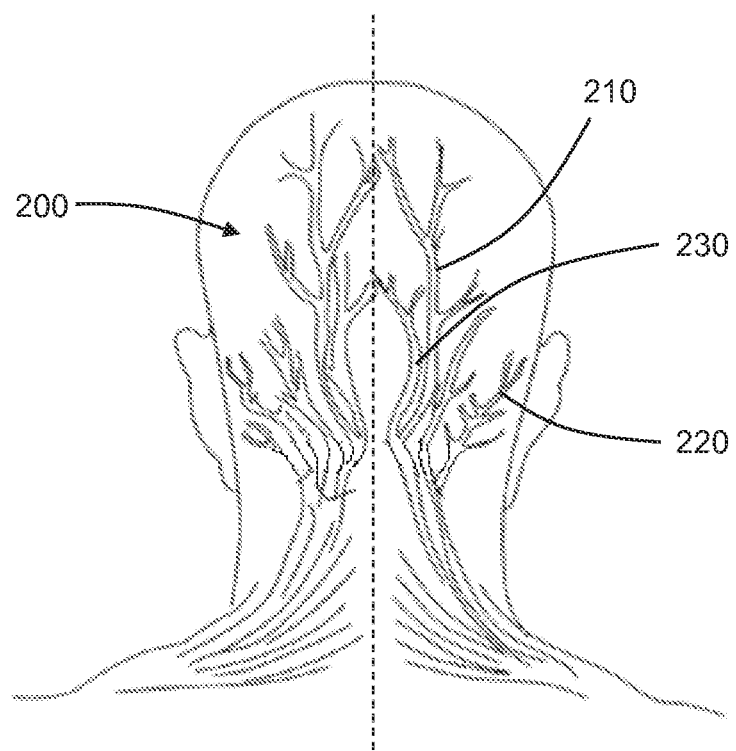
FIG. 9 is a schematic drawing showing occipital nerves of a subject.

Referring to FIG. 9, occipital nerves 200 of a subject are depicted in schematic form. As used herein, occipital nerve 200 includes the greater occipital nerve 210, the lesser occipital nerve 220 and the third occipital nerve 230. The greater and lesser occipital nerves are spinal nerves arising between the second and third cervical vertebrae (not shown). The third occipital nerve arises between the third and fourth cervical vertebrae. The portion of the occipital nerve 200 to which an electrical signal is to be applied may vary depending on the disease to be treated and associated symptoms or the stimulation parameters to be applied. In various embodiments, a portion of a lead that contains electrodes is placed to allow application of electrical signals to the occipital nerve 200 at a level of about C1 to about C2 or at a level in proximity to the base of the skull. The position of the electrode(s) may vary. In various embodiments, one or more electrodes are placed between about 1 cm and about 8 cm from the midline (dashed line in FIG. 9) to effectively provide an electrical signal to the occipital nerve 200. In embodiments, one lead is used to apply electrical stimulation to the left occipital nerve, and another lead is used to apply electrical stimulation to the right occipital nerve. In embodiments, one lead is used to apply electrical stimulation to both the left and right occipital nerves 200.

Figure 10:
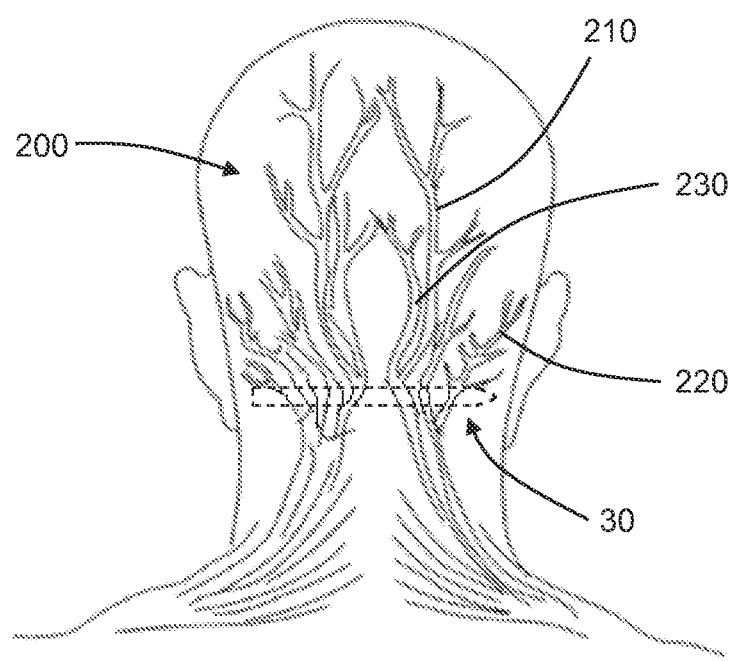
FIG. 10 is a schematic diagram showing an implanted lead positioned to apply electrical signals to an occipital nerve of a subject.
Figure 11A:
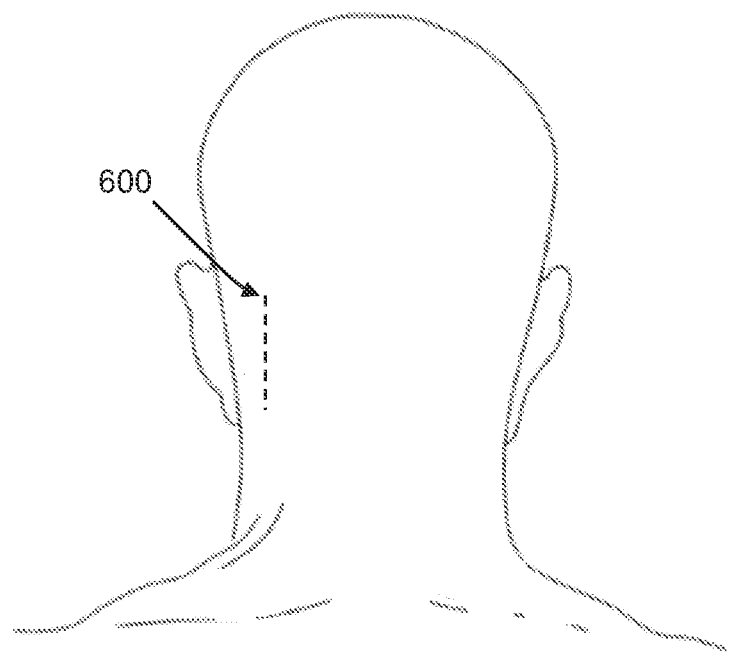
FIGS. 11A-E are schematic drawings illustrating a method for implanting a lead in a subject for purposes of applying electrical signals to an occipital nerve.
Figure 11B:
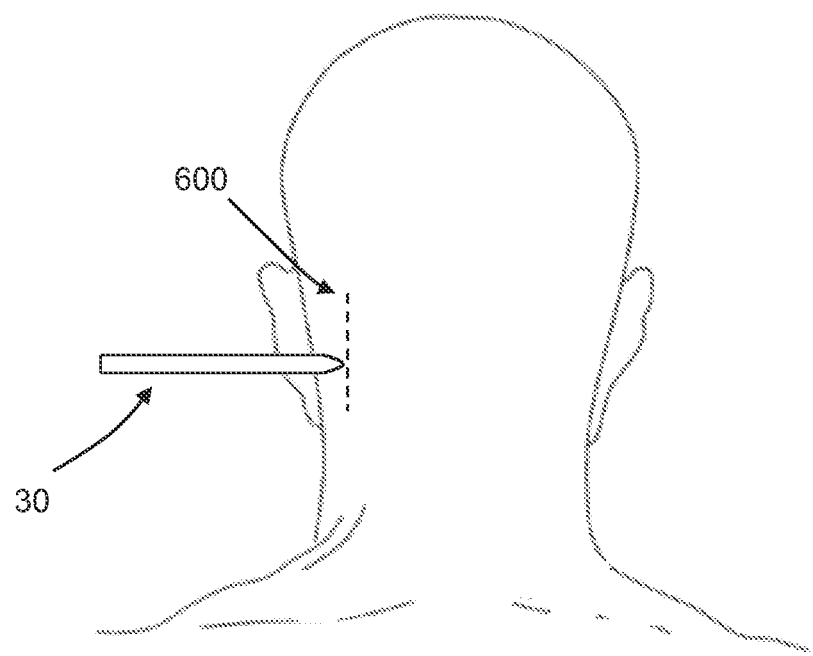
Figure 11C:
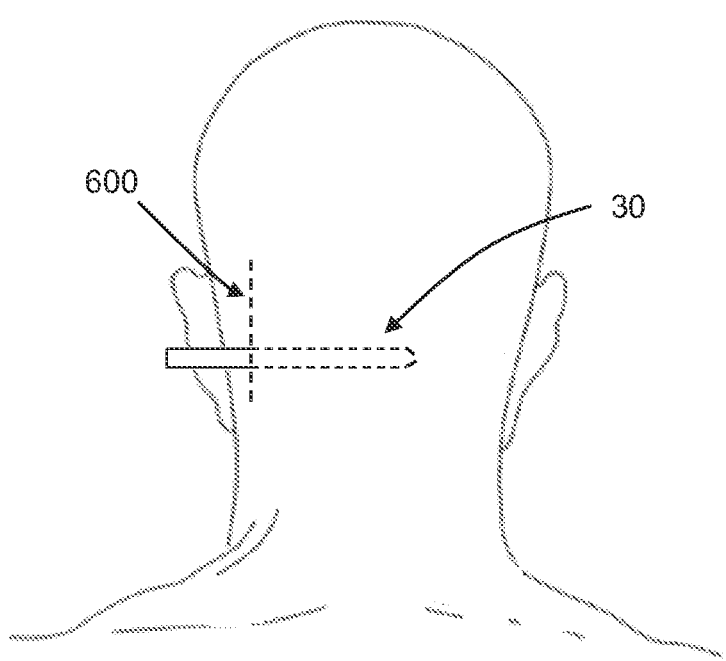
Figure 11D:
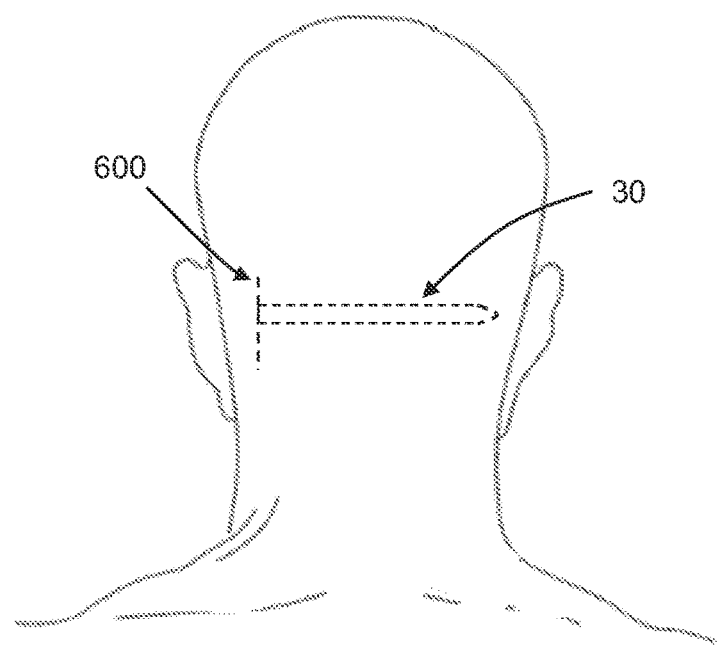
Figure 11E:
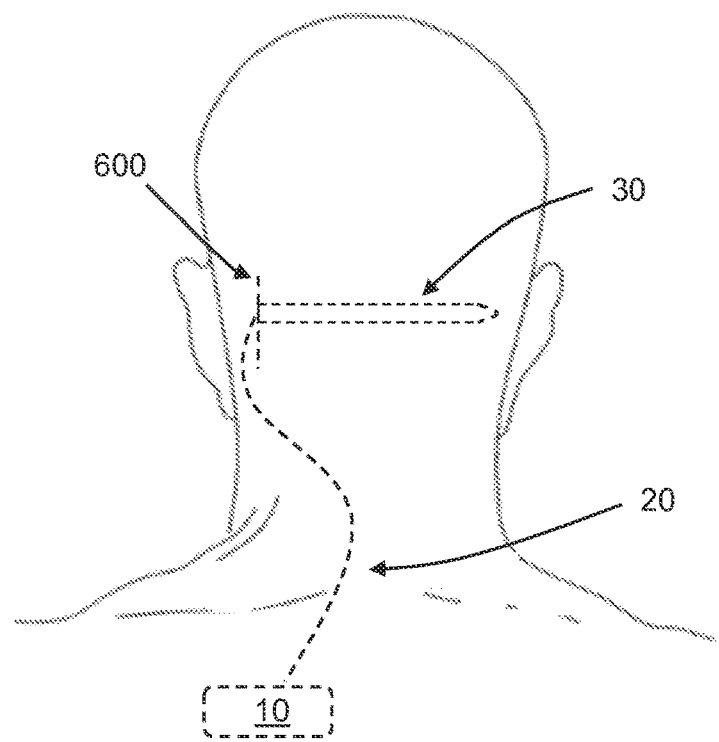

For example and with reference to FIG. 10, a lead 30 may be implanted such that electrodes (not shown in FIG. 10) are properly positioned to apply electrical signals to both the left and right occipital nerves 200. The lead 30 may be a lead as described with regard to FIG. 3, in which the lead has first and second electrode arrays with the most proximal electrode of the distal array being about 2 centimeters to 3 centimeters from the most distal electrode of the proximal array. The overall length of the arrays (from the most proximal electrode to the most distal electrode in an array) may be about 7 centimeters to about 10 centimeters. With such a lead, if the midline between the first and second electrode arrays is generally aligned with the midline of the back of the subject's head, the electrodes of the arrays should be properly positioned to apply electrical signals to the occipital nerves 200.

The leads described herein may be implanted in any suitable manner. One method for implanting a lead for purposes of applying electrical signals to an occipital nerve is shown in FIGS. 11A-E. As depicted, an incision 600 may be made in the back of a subject's head (e.g., at about the level of C1-C2 or the base of the skull). A lead 30 may be introduced through the incision 600 and advanced through subcutaneous tissue until electrodes of the lead 30 are properly positioned. The lead 30 may then be operably coupled to an implantable signal generator 10; e.g. via a lead extension 20.

The incision 600 depicted in FIGS. 11A-E is depicted as offset from the midline and the lead 30 is advanced beyond the midline. It will be understood that if two leads are employed for purposed of occipital nerve stimulation, where one is used for stimulating a right occipital nerve and another is used for stimulating a left occipital nerve, one incision may be made along the midline and the leads may be advanced in generally opposite directions to properly position electrodes of one lead with respect to the left occipital nerve and electrodes of the other lead with respect to the right occipital nerve.

Various embodiments of leads, systems and methods are described herein. Various aspects of some of the leads, systems and methods are summarized below.

In a $1^{st}$ aspect, an implantable medical lead comprises (i) a proximal end portion including a contact and having a proximal end; and (ii) a distal end portion including an electrode and having a distal end, the electrode being electrically coupled to the contact, wherein the distal end portion is generally flat or planar and sufficiently stiff to be pushed through subcutaneous tissue.

A $2^{nd}$ aspect is a lead of the $1^{st}$ aspect, wherein the distal end portion comprises a generally flat or planar body that is sufficiently stiff to be pushed through subcutaneous tissue.

A $3^{rd}$ aspect is a lead of the $2^{nd}$ aspect, wherein the body has a modulus of elasticity of 3000 psi or greater prior to being implanted in the patient.

A $4^{th}$ aspect is a lead of the $2^{nd}$ or $3^{rd}$ aspect, wherein the body is configured to become more compliant after being implanted in a patient relative to before being implanted in a patient.

A $5^{th}$ aspect is a lead of any of aspects 2-4, wherein the body is configured to have a modulus of elasticity of 3000 psi or greater prior to being implanted in the patient and to have a modulus of elasticity of 2500 psi or less after being implanted in the patient.

A $6^{th}$ aspect is a lead of any of aspects 2-4, wherein the body is formed from nylon, polycarbonate, or urethane.

A $7^{th}$ aspect is a lead of any of aspects 2-5, wherein the body is formed from a polymer selected from the group consisting of a polysaccharide, an alginate, a starch polymer, a temperature or fluid sensitive polyurethane, a hydrogel, and a temperature or fluid sensitive polyethylene oxide polymer.

An 8th aspect is a lead of any of aspects 2-5, wherein the body is formed from a temperature or fluid sensitive polyurethane.

A 9th aspect is a lead of the 1st or 2nd aspects, wherein the body is formed from nylon, polycarbonate, or urethane.

A 10th aspect is a lead of any of the first nine aspects, wherein the distal end portion. comprises a tapered distal end.

An 11th aspect is a lead according to any of the first ten aspects, wherein the generally flat or planar distal end portion extends to the proximal end portion.

A 12th aspect is a lead according to any of the first eleven aspects, wherein the generally flat or planar distal end portion comprises first and second electrode arrays, wherein each electrode of the first and second array are linearly arranged, wherein the space between adjacent electrodes in the first array is generally the same, wherein the space between adjacent electrodes in the second array is generally the same, and wherein the space between the most proximal electrode of the first array and the most distal electrode of the second array is between 2 cm and 16 cm.

A 13th aspect is a lead of the 12th aspect, wherein the electrodes of the first and second array comprise all of the electrodes of the lead.

A 14th aspect is a lead of any of aspects 1-13, wherein the subcutaneous tissue is hypodermis tissue that comprises mainly adipose tissue.

A 15th aspect is a system comprising (i) a lead according to any of aspects 1-14; and (ii) an implantable active electrical medical device operably couplable to the lead.

A 16th aspect is a system of the 15th aspect, wherein the active electrical medical device comprises an electrical signal generator.

A 17th aspect is a system of the 15th or 16th aspect, further comprising a lead extension configured to couple the lead to the implantable active electrical medical device.

An 18th aspect is a method comprising: (i) providing a lead according to any of aspects 1-13; and (ii) pushing the generally flat or planar portion to advance the distal end through subcutaneous tissue of the subject until the electrode is property positioned relative to a target area of the subject.

A 19th aspect is a method of the 18th aspect, wherein the subcutaneous tissue comprises mainly adipose tissue and the target area comprises an occipital nerve.

A 20th aspect is a method of the 18th aspect, wherein the target area comprises a peripheral nerve.

Thus, embodiments of SELF-TUNNELING LEAD are disclosed. One skilled in the art wilt appreciate that the leads, devices such as signal generators, systems and methods described herein can be practiced with embodiments other than those disclosed. The disclosed embodiments are presented for purposes of illustration and not limitation. One will also understand that components of the leads depicted and described with regard the figures and embodiments herein may be interchangeable.

What is claimed is:

1. An implantable medical lead comprising:
    a proximal end portion including a plurality of contacts and having a proximal end; and
    a distal end portion including an array of electrodes and having a distal end for tunneling and a generally flat body extending proximally from the distal end, each of the electrodes of the array being discretely electrically coupled to one of the plurality of contacts and the array of electrodes being exposed through a surface of the generally flat body along an array length,
    wherein the body of the distal end portion is sufficiently stiff to be pushed through subcutaneous tissue without use of an introducer and without use of a stylet.

2. The implantable medical lead of claim 1, wherein the distal end portion is sufficiently stiff to be pushed through subcutaneous tissue.

3. The implantable medical lead of claim 2, wherein the body has a modulus of elasticity of 3000 psi or greater prior to being implanted in the patient.

4. The implantable medical lead of claim 2, wherein the body is configured to become more compliant after being implanted in a patient relative to before being implanted in a patient.

5. The implantable medical lead of claim 2, wherein the body is configured to have a modulus of 3000 psi or greater prior to being implanted in the patient and to have a modulus of elasticity of 2500 psi or less alter being implanted in the patient.

6. The implantable medical lead of claim 2, wherein the body is formed from nylon, polycarbonate, or polyurethane.

7. The implantable medical lead of claim 2, wherein the body is formed from a polymer selected from the group consisting of a polysaccharide, an alginate, a starch polymer, a temperature or fluid sensitive polyurethane, a hydrogel, and a temperature or fluid sensitive polyethylene oxide polymer.

8. The implantable medical lead of claim 2, wherein the body is formed from a temperature or fluid sensitive polyurethane.

9. The implantable medical lead of claim 1, wherein the distal end portion comprises a body formed from nylon, polycarbonate, or polyurethane.

10. The implantable medical lead of claim 1, wherein the distal end portion comprises a tapered distal end.

11. The implantable medical lead of claim 1, wherein the generally flat distal end portion extends to the proximal end portion.

12. The implantable medical lead of claim 1, wherein the generally flat distal end portion comprises first and second electrode arrays, wherein each electrode of the first and second array are linearly arranged, wherein the space between adjacent electrodes in the first array is generally the same, wherein the space between adjacent electrodes in the second array is generally the same, and wherein the space between the most proximal electrode of the first array and the most distal electrode of the second array is between 2 cm and 16 cm.

13. The implantable medical lead of claim 12, wherein the electrodes of the first and second array comprise all of the electrodes of the lead.

14. The implantable medical lead of claim 1, wherein the subcutaneous tissue is hypodermis tissue that comprises mainly adipose tissue.

15. A system comprising:
    a lead according to claim 1; and
    an implantable active electrical medical device operably couplable to the lead.

16. The system of claim 15, wherein the active electrical medical device comprises an electrical signal generator.

17. The system of claim 15, further comprising a lead extension configured to couple the lead to the implantable active electrical medical device.

18. The implantable medical lead of claim 1, wherein the generally flat body comprises a planar body having a constant width along its length as seen from a first view and the distal end portion comprises a tapered distal end as seen from a second view orthogonal to the first view.

* * * * *